United States Patent [19]

Schneider et al.

[11] Patent Number: 4,577,978
[45] Date of Patent: Mar. 25, 1986

[54] FIELD TEST FOR DETERMINING WATER IN OIL

[75] Inventors: Julian R. Schneider; Gene A. Pullen, both of Houston, Tex.

[73] Assignee: Shell Oil Company, Houston, Tex.

[21] Appl. No.: 663,293

[22] Filed: Oct. 22, 1984

[51] Int. Cl.$^4$ .................. G01N 25/00; G01N 25/10
[52] U.S. Cl. ............................ 374/45; 374/54; 73/61.3; 436/40
[58] Field of Search .................. 374/16, 17, 27, 45, 374/54; 73/61.3, 61.1 R; 116/216; 436/40; 99/342; 208/187

[56] References Cited

U.S. PATENT DOCUMENTS

| | | | |
|---|---|---|---|
| 1,747,742 | 2/1930 | Stein | 374/27 |
| 3,695,095 | 10/1972 | Lineberg | 374/54 |
| 3,926,038 | 12/1975 | Wunning et al. | 73/61.3 |
| 3,971,248 | 7/1976 | Christensen | 73/61.1 R |
| 4,250,738 | 2/1981 | Huch | 374/45 |
| 4,251,809 | 2/1971 | Cheney | 73/61.1 R |
| 4,484,823 | 11/1984 | Peuker | 374/54 |

FOREIGN PATENT DOCUMENTS

| | | | |
|---|---|---|---|
| 0102409 | 3/1984 | European Pat. Off. | 374/16 |
| 0223049 | 12/1983 | Japan | 73/61.1 R |

Primary Examiner—Charles Frankfort
Assistant Examiner—Thomas B. Will
Attorney, Agent, or Firm—Kimbley L. Muller

[57] ABSTRACT

A semi-quantitative method for determining the amount of water in contaminated oil samples wherein a small sample of contaminated oil is placed in one or more compartments of a container. An equal size sample of reference oil of the same composition as the test oil, but containing a known quantity of water, is placed in one or more compartments of said container. The container is then heated rapidly and bubbles formed in the contaminated oil are compared with bubbles formed in the reference oil, thereby bracketing the water content rapidly (less than 5 minutes) with reasonable accuracy.

5 Claims, 5 Drawing Figures

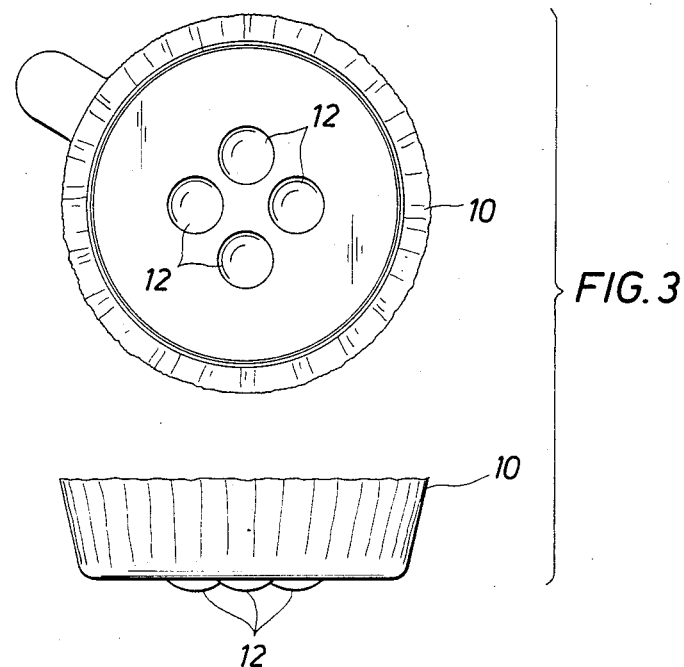
FIG. 3
FIG. 1
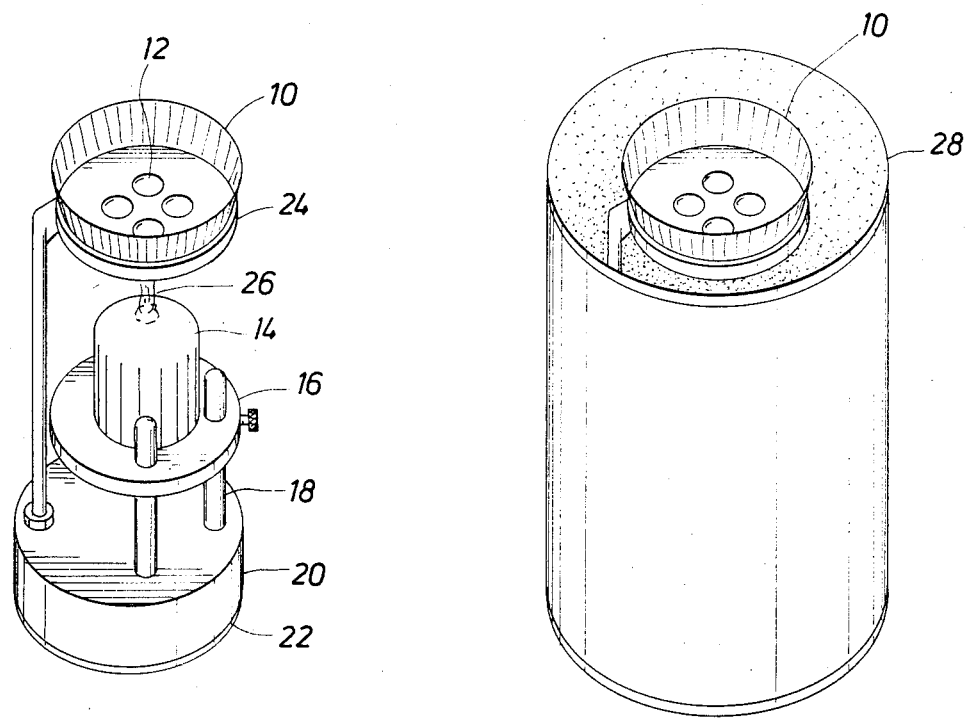
FIG. 2

FIG. 4
FIG. 5
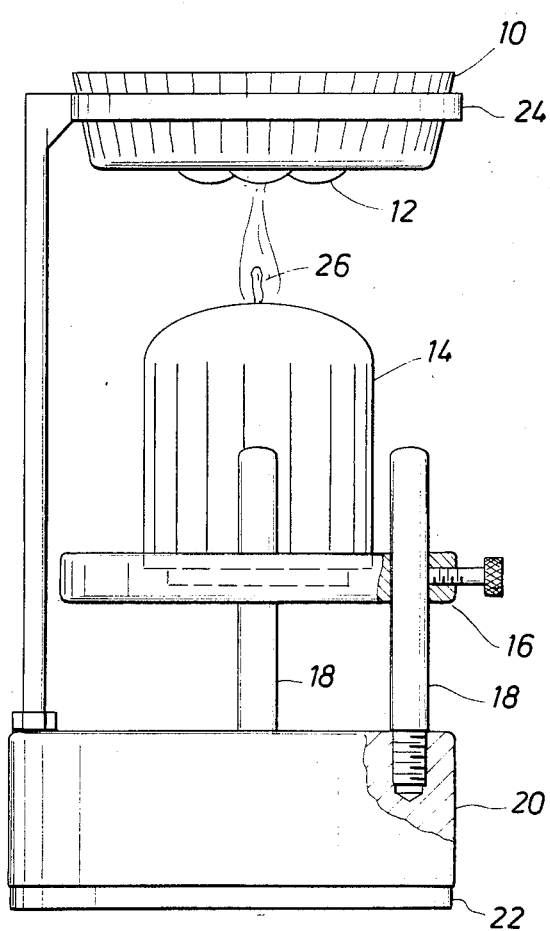
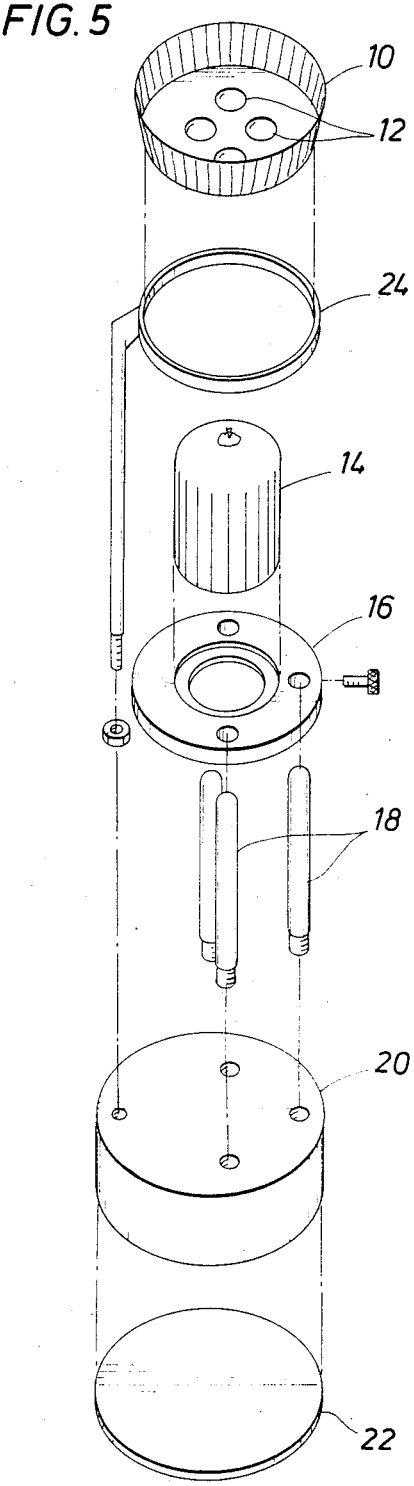

FIELD TEST FOR DETERMINING WATER IN OIL

BACKGROUND OF THE INVENTION

This invention relates to a semi-quantitative method for determining small quantities of water (generally less than about 1%v) in oil. The invention particularly relates to the determination of water in hydraulic and lubricating oils.

In the past, great emphasis has been placed on ensuring that the condition of new hydraulic and automotive oils is satisfactory, i.e., that their composition and viscosity are correct, and that their dirt and water contents are negligible. However, once in service, these oils are often subjected to contamination from both dirt and water as well as subject to slow deterioration due to additive depletion and oxidation. Although these developments can be readily assessed in the laboratory, it is time consuming and expensive to convey samples to and from a service laboratory. It is therefore desirable to devise equipment suitable for simple, cheap, rapid and accurate on-the-spot monitoring of the condition of mineral-oil-based oils from which their expected future service life might be assessed.

For years, many automotive and industrial equipment users have used a so-called "crackle" test (often referred to as the snap, pop and crackle test) to check for water in lubricants. The test involves dropping a sample of the questionable oil on a hot surface. Depending on the temperature involved, a dry oil will smoke, while a wet oil will "crackle". A safer method than using a hot surface to drop the oil on, is one where one or two drops of oil are placed on aluminum foil and a match flame is slowly applied to the under surface of the foil. Other methods include the use of a spoon, aluminum weighing dish, etc. The above methods, however, are non-quantitative, and only indicate the presence of water.

A study of several commercially available test kits has revealed that some were totally inadequate for use in determining the water content of oils, while others were too time consuming.

One such kit was found to be non-quantitative and very crude. It comprises heating a "hot plate" (bent 18 gauge steel clipped to and held above a small spirit lamp heater) to above 100° C. and placing a drop of oil in an indent in this hotplate. The amount of moisture present is indicated by the intensity of crackling and frothing as the water boils off. However, since degeneration of hydraulic equipment can begin at quite low water levels, it is essential that these levels be accurately determined.

The "Oil Type Speedy Moisture Tester", manufactured by Thomas Ashworth and Co. Ltd., Burnley, Lancs, U.K. was found to be lacking in accuracy and general usefulness. In common with most of the kits examined the "Speedy" relies upon a water finding reagent, calcium carbide in this case, reacting with, and producing a pressure rise in direct proportion to, water content. The water content of the oil can be read directly from a pre-calibrated gauge. For the detection of water in oil it is recommended that the sample be placed in the apparatus in the presence of a dry sand adsorbent (presumably this is to make the water more accessible for reaction with the non-soluble carbide). When the procedure outlined in the "Speedy" literature was followed, inconsistent and inaccurate results were obtained.

We have developed a method which overcomes some of the limitations of prior art water test kits.

SUMMARY OF THE INVENTION

The present invention represents a rapid, simple field test for the determination of water in industrial and lubricating oils. Equipment required for the test is readily available. The test requires less than 5 minutes to complete. Test oils are compared to reference oils of essentially the same composition, but which contain known amounts of water. A small, measured amount of test oil is placed in one or more compartments, or indentations, of a suitable heating container, preferably a weighing dish. An equal amount of reference oil is placed in one or more additional compartments or indentations of the heating container, which is then heated rapidly e.g., with a warming candle, so that the temperatures of said test oil and said reference oil are approximately equal. The water content of the test oil is determined by comparing the rate of bubble formation during heating to that in the reference oil. Greater bubble formation indicates more water.

BRIEF DESCRIPTION OF THE DRAWING

The present invention will be more easily understood from the following detailed description of preferred embodiment when taken in conjunction with the attached drawings in which:

FIG. 1 is an isometric view of an apparatus constructed according to this invention.

FIG. 2 is an isometric view of the apparatus with a flame stabilizing shroud in place.

FIG. 3 is a side view and top view of an aluminum weighing dish.

FIG. 4 is a side view of the apparatus.

FIG. 5 is an expanded isometric view of individual parts of the apparatus.

DESCRIPTION OF PREFERRED EMBODIMENT

The list of equipment and the test procedures described below are that of a preferred embodiment of the invention. It will be readily apparent to those skilled in the art that substitutions may be made for several of the equipment items and procedural steps without departing from the essence of the invention.

EQUIPMENT REQUIRED

Aluminum weighing dishes
Warming candle $1\frac{3}{8}''$ diameter, $1\frac{1}{2}''$ to $2''$ tall
Apparatus to hold aluminum dish with adjustable base for setting proper candle flame height
Shield for stabilizing candle flame, e.g., 1 lb. coffee tin with top and bottom removed
Indent mold capable of making four evenly-spaced indentations (capable of holding two drops or 50 microliter each of oil) in aluminum weighing dish
Five reference oils, as follows:
  Dry, 0.10. 0.20, 0.50, 1.00 percent volume water
$\frac{1}{8}''$ diameter rod, $6''$ long for dispensing oil drops. Precision of test can be improved using a fixed stroke piston pipette, such as the Eppendorf 3130 capable of dispensing 50 microliters of oil
$3''$ diameter safety cover in event oil flares
Equipment necessary to prepare reference oils in the field

PROCEDURES

I. Procedure for Making Reference Samples

1. Obtain a one quart sample of new/used oil and check for presence of water. If water is indicated, heat the oil to about 220° F. and check periodically until procedure indicates the oil is dry. After heating, allow the oil to cool to room temperature.

2. To make 100 ml reference samples, place the required amount of water in a 4 oz. wide mouth jar using a syringe graduated in 0.5 ml divisions. Then add the required amount of oil using a 50 ml. syringe. Cap the bottle and shake vigorously for about two minutes.

II. Bracketing Test Oil Sample

1. Place aluminum weighing dish 10 in indent mold (not shown). Using round end of a ballpoint pen, make four 12 indentions in dish.

2. Place warming candle 14 in adjustable candle holder plate, 16. The plate 16 is movable vertically along three guides 18 which are supported by a base 20, preferably resting on skid proof material 22. Place aluminum dish 10 in dish holder circle 24. Cut candle wick 26 so only ¼" is above wax. Light candle 14 and adjust until tip of flame is touching bottom of aluminum dish 10. Make sure flame tip is in middle of the four indentions (use flame stabilizing shield 28 for final adjustment).

3. Blow out candle flame.
4. Remove stabilizing shield 28.
5. Remove aluminum dish 10 when cool.
6. Place two drops or 50 microliters of test oil in one indention. Place two drops or 50 microliters of the 0.5%v water reference oil in opposite indention.
7. Light candle 14 and place stabilizing shield 28 around apparatus.
8. Set aluminum dish 10 flush in holder circle 24.
9. Note bubbles in oils. If test oil bubbles more than reference oil, repeat test using unused indentions and 1.0%v water reference oil and test oil.
10. If test oil bubbles more than reference oil—water content is greater than 1%v.
11. If test oil bubbles less than reference oil, the operator evaluation of the results indicated by the two tests will place the water content closer to the 0.5% or 1.0% or in the middle=0.75%.

The bracketing procedure will work in the reverse (0.5%-0.2%, etc.) depending on initial results with the 0.5% reference oil. If oil is dry—no bubbles will appear and the test is complete. Note: In this procedure the amount of bubbling is used as an indication of the presence of water in test oil. Therefore, DO NOT place an ear close to test device to listen for crackle—sample may ignite if fuel dilution present. In the event the sample ignites—immediately place safety cover over shield. Testing dish should not be removed until it has cooled.

III. "GO—NO GO" PROCEDURE

1. Follow steps 1-5 in bracketing procedure.
2. Place two drops of oil to be tested in one indention. Place two drops of reference oil (blended to condemnation limit) in opposite indention.
3. Follow steps 7 and 8 in bracketing procedure.
4. Note bubble reaction of test oil. If less than reference oil—it's "go"; if reaction is the same or greater than reference oil—its "no go".

WARNING

1. Because of open candle flame, test should be conducted in well ventilated area away from combustibles.
2. Tester should avoid breathing fumes and/or mist discharged as a result of heating oil at very high temperature (candle flame can reach 1,000° F.).

What is claimed is:

1. A rapid field method for determining small amounts of water in industrial and lubricating oils which comprises:
   placing a measured sample of a test oil in one or more compartments of a suitable heating container;
   placing an equal amount of a reference oil containing a known quantity of water in one or more additional compartments of said heating container;
   heating said container rapidly to heat said test oil and said reference oil and to thereby increase the temperature of said reference oil and said test oil to approximately equal temperatures and to generate a quantity of bubbles rising through said reference oil and said test oil; and
   observing said quantity of bubbles generated in said test oil and said reference oil to provide a relative indication of the amount of water in said test oil.

2. The method of claim 1 wherein said test oil and said reference oil are essentially the same oil compositions, except for the known water content present in said reference oil.

3. The method of claim 2 wherein five reference oils are prepared containing a range of water contents selected from the group consisting of 0.0, 0.1, 0.2, 0.5 and 1.0 percent volume.

4. The method of claim 1 wherein said test oil is compared to said reference oil containing said known quantity of water, said water content being the known maximum volume of water permissible in said reference oil, and the test oil is observed to pass if fewer bubbles are generated in the test oil during heating than are generated in said reference oil.

5. A rapid field test method for semi-quantitatively determining up to about 1%v water in industrial or automotive lubricating oils which comprises:
   placing about 50 microliters of said industrial or automotive lubricating oil into an indentation of a heating dish having four equally spaced indentations in the bottom thereof;
   placing an equal amount of a first reference oil to be tested having the same composition as said industrial or automotive lubricating oil, but containing a first known quantity of water, into an opposite indentation of said heating dish;
   placing a warming candle having a flame tip beneath said dish so that when said candle is ignited, the flame tip from said candle is formed and is situated to touch said bottom of said dish in the middle of said four equally spaced indentations;
   igniting said candle and placing a shield around said candle to stabilize said formed flame tip and to thereby provide even heating to said oils in said heating dish and to thereby form bubbles arising through said oils;
   observing bubbles formed in said oils to compare said oil bubbles in said reference oil and said industrial or automotive lubricating oil; wherein,
   if more bubbles are present in said industrial or automotive lubricating oil than present in said first reference oil, repeat the test method using unused indentations and a second reference oil containing a second known quantity of and more water than was present in said first reference oil; or if fewer bubbles are present in said industrial or said automotive oil than said first reference oil, repeat the test method using unused indentations and a third reference oil containing a third known quantity of and less water than the first reference oil; and continuing this procedure until a reasonable match of bubble formation is obtained between said industrial or automotive oil and said reference oil.

* * * * *